US008869029B2

(12) United States Patent  (10) Patent No.: US 8,869,029 B2
Ying et al. (45) Date of Patent: *Oct. 21, 2014

(54) HANDHELD DEVICE GRAPHICAL USER INTERFACES FOR DISPLAYING PATIENT MEDICAL RECORDS

(75) Inventors: Alan J. Ying, Durham, NC (US); William T. Lawson, Apex, NC (US); Mark Farnsworth, Raleigh, NC (US); Jeffrey Keating, Apex, NC (US)

(73) Assignee: Truven Health Analytics Inc., Chicago, IL (US)

( * ) Notice: Subject to any disclaimer, the term of this patent is extended or adjusted under 35 U.S.C. 154(b) by 275 days.

This patent is subject to a terminal disclaimer.

(21) Appl. No.: 11/970,177

(22) Filed: Jan. 7, 2008

(65) Prior Publication Data

US 2008/0263477 A1  Oct. 23, 2008

Related U.S. Application Data

(63) Continuation of application No. 10/101,577, filed on Mar. 20, 2002, now Pat. No. 7,343,565.

(51) Int. Cl.
  *G06F 3/00* (2006.01)
  *G06F 3/048* (2013.01)
  *G06F 3/0488* (2013.01)
  *G06F 3/0482* (2013.01)
  *G06F 19/00* (2011.01)

(52) U.S. Cl.
  CPC .......... *G06F 3/0488* (2013.01); *G06F 3/04886* (2013.01); *G06F 19/3418* (2013.01); *G06F 19/327* (2013.01); *G06F 19/322* (2013.01); *G06F 3/0482* (2013.01); *G06F 19/3406* (2013.01)
  USPC ........................................... 715/709; 715/767

(58) Field of Classification Search
  CPC ................................. G06F 3/00; G06F 3/048
  USPC ................................................ 715/709, 767
  See application file for complete search history.

(56) References Cited

U.S. PATENT DOCUMENTS 5,128,672 A   7/1992   Kaehler
5,267,155 A   11/1993  Buchanan et al.
(Continued)

OTHER PUBLICATIONS

Screen Dumps of EAST, v. 2.0.1, U.S. Patent & Trademark Office, (1999), 4 p.
(Continued)

*Primary Examiner* — Doon Chow
*Assistant Examiner* — Le Nguyen
(74) *Attorney, Agent, or Firm* — Plumsea Law Group, LLC

(57) ABSTRACT

Ergonomic graphical user interfaces (GUIs) for displaying medical record information obtained from various sources within handheld devices are provided. A GUI for display within a touch screen display of a handheld device includes adjacent first and second portions. A list of patient names is displayed within the first portion of the GUI, along with medical facility location information, means for indicating when new clinical data for a patient is available, means for removing patient names from the displayed list, and means for sorting the displayed list of patient names. A plurality of ergonomically designed GUI controls are displayed within the second portion of the GUI. Each of these GUI controls has a width that is between about 15% and 75% of a width of the display, and a height that is between about 15% and 75% of a height of the display. According to embodiments, a GUI for display within a touch screen display of a handheld device includes adjacent first and second portions, wherein the second portion has a height that is between about 30% and 70% of a height of the GUI. Information for a respective patient is displayed within the first portion and includes patient identification and location information. At least some of the displayed information is responsive to user touching for displaying additional patient information. Various GUI controls are displayed within the second portion, and is responsive to user touching for performing various functions. Each of the GUI controls in the second portion has a width that is between about 15% and 75% of a width of the second portion, and a height that is between about 15% and 75% of a height of the second portion.

18 Claims, 8 Drawing Sheets

(56) References Cited

U.S. PATENT DOCUMENTS

| | | | |
|---|---|---|---|
| 5,327,341 A | 7/1994 | Whalen et al. | |
| 5,659,741 A | 8/1997 | Eberhardt | |
| 5,758,095 A * | 5/1998 | Albaum et al. | 705/2 |
| 5,772,585 A | 6/1998 | Lavin et al. | |
| 5,778,404 A * | 7/1998 | Capps et al. | 715/234 |
| 5,823,948 A | 10/1998 | Ross et al. | |
| 5,832,450 A * | 11/1998 | Myers et al. | 705/3 |
| 5,845,255 A * | 12/1998 | Mayaud | 705/3 |
| 5,880,724 A | 3/1999 | Bertram et al. | |
| 5,903,889 A | 5/1999 | De La Huerga | |
| 5,924,074 A * | 7/1999 | Evans | 705/3 |
| 5,950,168 A | 9/1999 | Simborg et al. | |
| 5,995,965 A | 11/1999 | Experton | |
| 6,067,524 A | 5/2000 | Byerly et al. | |
| 6,169,538 B1 | 1/2001 | Nowlan et al. | |
| 6,208,344 B1 | 3/2001 | Holzman et al. | |
| 6,208,974 B1 | 3/2001 | Campbell et al. | |
| 6,263,330 B1 | 7/2001 | Bessette | |
| 6,405,238 B1 * | 6/2002 | Votipka | 709/203 |
| 6,421,066 B1 * | 7/2002 | Sivan | 715/712 |
| 6,476,833 B1 | 11/2002 | Moshfeghi | |
| 6,522,347 B1 * | 2/2003 | Tsuji et al. | 715/848 |
| 6,678,397 B1 | 1/2004 | Ohmori et al. | |
| 6,707,942 B1 * | 3/2004 | Cortopassi et al. | 382/186 |
| 6,734,880 B2 * | 5/2004 | Chang et al. | 715/738 |
| 6,779,119 B1 * | 8/2004 | Moshfeghi et al. | 726/23 |
| 6,879,996 B1 * | 4/2005 | Laves | 709/206 |
| 6,972,775 B1 * | 12/2005 | Haakonsen | 345/646 |
| 7,010,616 B2 * | 3/2006 | Carlson et al. | 709/246 |
| 7,013,324 B1 * | 3/2006 | Sugano et al. | 709/203 |
| 7,222,156 B2 * | 5/2007 | Gupta et al. | 709/206 |
| 7,343,565 B2 | 3/2008 | Ying et al. | |
| 7,426,475 B1 * | 9/2008 | Tangellapally et al. | 705/3 |
| 7,447,643 B1 * | 11/2008 | Olson et al. | 705/2 |
| 7,844,666 B2 * | 11/2010 | Horvitz et al. | 709/206 |
| 2002/0007284 A1 * | 1/2002 | Schurenberg et al. | 705/2 |
| 2002/0010626 A1 * | 1/2002 | Agmoni | 705/14 |
| 2002/0019751 A1 | 2/2002 | Rothschild et al. | |
| 2002/0040305 A1 * | 4/2002 | Nakatsuchi et al. | 705/2 |
| 2002/0057285 A1 * | 5/2002 | Nicholas, III | 345/700 |
| 2002/0169637 A1 * | 11/2002 | Akers et al. | 705/3 |
| 2002/0184325 A1 * | 12/2002 | Killcommons et al. | 709/206 |
| 2003/0036683 A1 * | 2/2003 | Kehr et al. | 600/300 |
| 2003/0046113 A1 * | 3/2003 | Johnson et al. | 705/3 |
| 2003/0095150 A1 * | 5/2003 | Trevino et al. | 345/810 |
| 2004/0204837 A1 * | 10/2004 | Singleton | 701/209 |
| 2006/0218501 A1 * | 9/2006 | Wilson et al. | 715/769 |

OTHER PUBLICATIONS

"U.S. Appl. No. 10/101,577, Advisory Action mailed Oct. 11, 2006", 2 pgs.

"U.S. Appl. No. 10/101,577, Final Office Action mailed Jun. 20, 2008", 30 pgs.

"U.S. Appl. No. 10/101,577, Final Office Action mailed Apr. 5, 2006", 30 pgs.

"U.S. Appl. No. 10/101,577, Non-Final Office Action mailed Nov. 1, 2006", 31 pgs.

"U.S. Appl. No. 10/101,577, Notice of Allowance mailed Oct. 18, 2007", 9 pgs.

"U.S. Appl. No. 10/101,577, Response filed Apr. 2, 2007 to Non-Final Office Action mailed Nov. 1, 2006", 31 pgs.

"U.S. Appl. No. 10/101,577, Response filed Aug. 15, 2007 to Final Office Action mailed Jun. 20, 2007", 8 pgs.

"U.S. Appl. No. 10/101,577, Response filed Sep. 6, 2006 to Final Office Action mailed Apr. 5, 2006", 29 pgs.

"U.S. Appl. No. 10/101,577, Response filed Oct. 5, 2006 to Final Office Action mailed Apr. 5, 2006", 31 pgs.

* cited by examiner

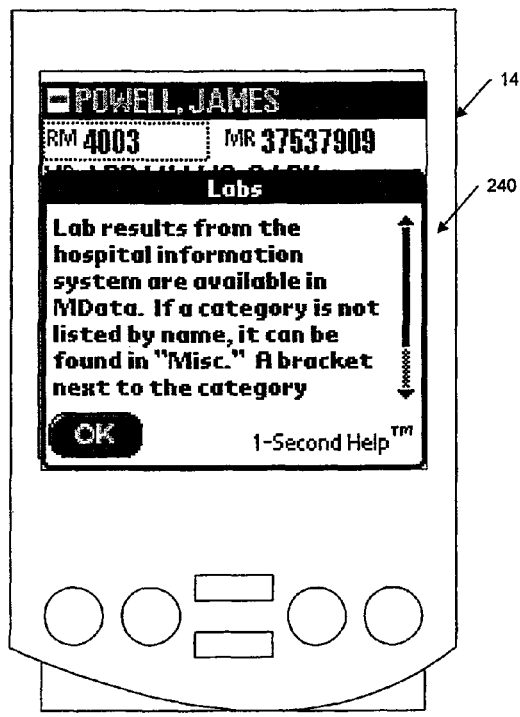
Fig. 19
Fig. 20
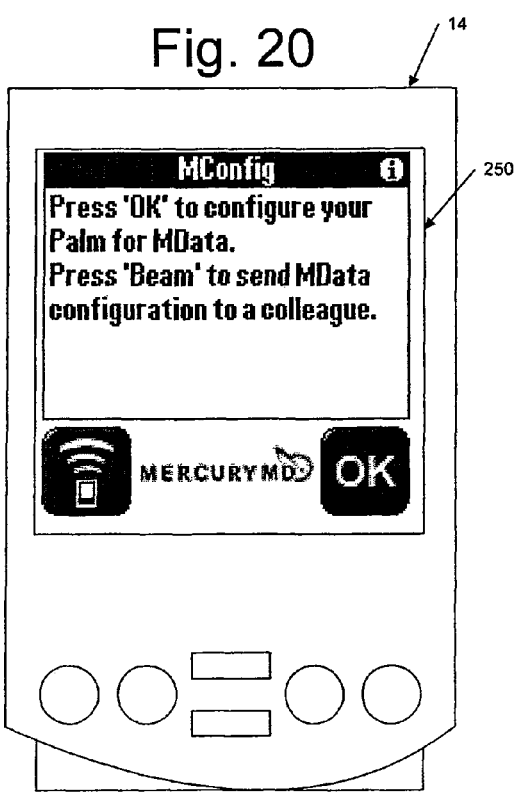

HANDHELD DEVICE GRAPHICAL USER INTERFACES FOR DISPLAYING PATIENT MEDICAL RECORDS

This application is a continuation of Ser. No. 10/101,577 U.S. Pat. No. 7,343,565, filed on Mar. 20, 2002 and issued on Mar. 11, 2008, which is incorporated herein by reference.

RESERVATION OF COPYRIGHT

A portion of the disclosure of this patent document contains material to which a claim of copyright protection is made. The copyright owner has no objection to the facsimile reproduction by anyone of the patent document or the patent disclosure, as it appears in the Patent and Trademark Office patent file or records, but reserves all other rights whatsoever.

FIELD OF THE INVENTION

The present invention relates generally to medical records and, more particularly, to user interfaces for displaying medical records.

BACKGROUND OF THE INVENTION

To effectively treat patients, healthcare providers often require access to various kinds of patient information from various sources. Patient information that healthcare providers may need access to may include family illness information, physical examination information, medical diagnoses, laboratory data, x-ray reports, special studies, prescriptions, medications, therapies, consultation reports, and records from previous hospitalizations and clinic visits. Various computer systems have been developed to obtain and present patient information to healthcare providers. Unfortunately, a complaint often heard among healthcare providers utilizing these computer systems is that access to patient information can be time consuming and difficult.

Conventionally, health care providers are required to log on to a computer system via a desktop computer and navigate through one or more complex programs in order to access medical records stored within one or more data sources. Once a data source is accessed, the patient information contained therein typically requires some amount of collating and transcribing in order to provide the patient information into a usable format. Accordingly, healthcare providers are often required to spend a great deal of time locating and formatting patient information for use.

In addition, healthcare computer systems in healthcare facilities typically are not located near patients. For example, computer access to patient information typically is not available to a healthcare provider in a patient's room. As such, healthcare providers may not be able to access information about a patient as he/she is visiting with a patient.

Increasingly, healthcare providers are utilizing handheld/wireless devices, such as personal digital assistants (PDAs) to perform a variety of computing and communication functions, including sending and retrieving e-mail, Web browsing, and data-sharing applications over the Internet, intranet and/or corporate networks. Handheld device operating systems typically utilize graphical user interfaces (GUIs) that allow users to perform various functions. For example, on a Palm® OS device, a user interacts with graphical representations (e.g., application icons) and controls (e.g., buttons, scroll bars, etc.) referred to herein as GUI controls. These GUI controls often perform various functions in response to physical touching by a user (e.g., touching or tapping via a finger or stylus). Unfortunately, medical record data is typically not accessible via handheld devices. Moreover, patient information is conventionally maintained in one or more formats that is not conducive to display via a handheld device.

Accordingly, there is a need for improved, less time-consuming ways of allowing healthcare providers to access patient information from various sources, and from various locations. In addition, there is a need for improved ways of presenting patient information to healthcare providers via various handheld devices.

SUMMARY OF THE INVENTION

In view of the above, the present invention provides ergonomic graphical user interfaces (GUIs) for displaying medical record information obtained from various sources within handheld devices. According to embodiments, a GUI for display within a touch screen display of a handheld device includes adjacent first and second portions. A list of patient names is displayed within the first portion of the GUI, along with medical facility location information, means for indicating when new clinical data for a patient is available, means for removing patient names from the displayed list, and means for sorting the displayed list of patient names. A plurality of ergonomically designed GUI controls are displayed within the second portion of the GUI. Each of these GUI controls has a width that is between about 15% and 75% of a width of the display, and a height that is between about 15% and 75% of a height of the display.

A first GUI control displayed within the second portion of the GUI is responsive to user touching for adding patient names to the displayed list of patient names. A second GUI control displayed within the second portion of the GUI is responsive to user touching for downloading clinical data from a plurality of medical facility data sources to the handheld device. A third GUI control displayed within the second portion of the GUI is responsive to user touching for displaying information about new clinical data for patients.

According to embodiments, a GUI for display within a touch screen display of a handheld device includes adjacent first and second portions, wherein the second portion has a height that is between about 30% and 70% of a height of the GUI. Information for a respective patient is displayed within the first portion and includes patient identification and location information. At least some of the displayed information is responsive to user touching for displaying additional patient information. A first GUI control is displayed within the second portion, and is responsive to user touching for displaying test results categorized from a preselected list of clinical tests performed on a patient identified within the first portion of the GUI. A second GUI control is displayed within the second portion, and is responsive to user touching for displaying clinical test results for the patient obtained within a selectable preceding time period. A third GUI control is displayed within the second portion, and is responsive to user touching for displaying a list of medications prescribed to the patient identified within the first portion of the GUI. A fourth GUI control is displayed within the second portion, and is responsive to user touching for launching an application (e.g., a charge capture application, decision support algorithm, etc.) within the first portion that is associated with the patient information displayed within the first portion. Various types of applications may be launched, without limitation. Each of the first, second, third, and fourth GUI controls has a width that is between about 15% and 75% of a width of the second portion, and a height that is between about 15% and 75% of a height of the second portion.

Embodiments of the present invention can be advantageous because healthcare providers can obtain up-to-date accurate information about patients without having to cull the information from multiple data sources using conventional methods. As such, healthcare providers can spend more time with patients, which may lead to improved patient care and shortened length of stay. In addition, embodiments of the present invention can decrease medical errors due to illegibility, incompleteness, and poor data availability, and can reduce redundant testing through better order management.

Handheld devices according to embodiments of the present invention can increase physician mobility without compromising accessibility to data. Moreover, GUIs according to embodiments of the present invention are easy to use and learn by healthcare providers.

BRIEF DESCRIPTION OF THE DRAWINGS

FIGS. 3-20 are various graphical user interfaces (GUIs) according to embodiments of the present invention.

DETAILED DESCRIPTION OF THE INVENTION

Figure 1:
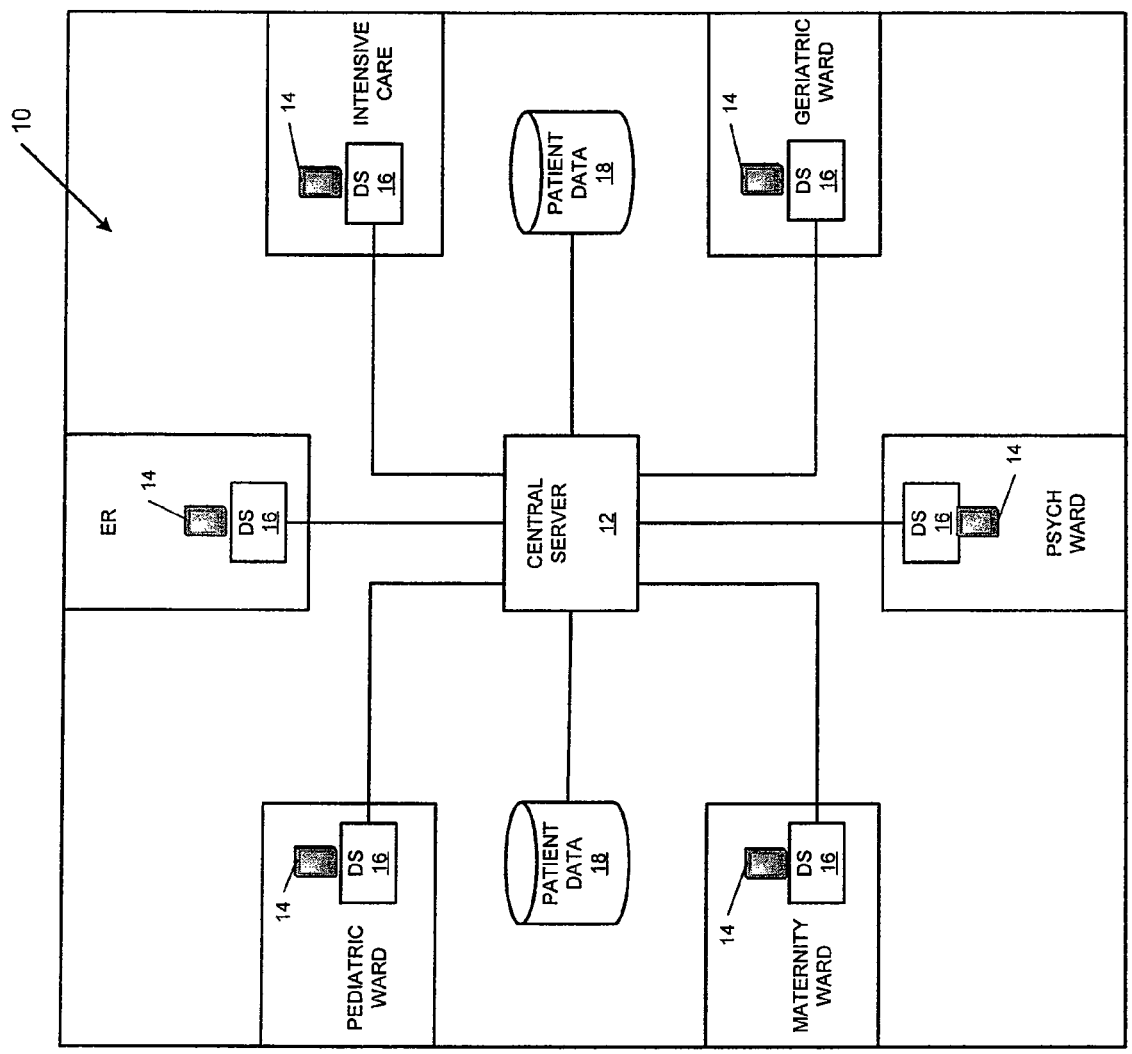
FIG. 1 is a block diagram that illustrates a data processing system according to embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention can be embodied as graphical user interfaces for handheld devices, as well as methods, computer program products, and data processing systems for obtaining medical record data from one or more sources and displaying the obtained medical record data via ergonomic GUIs within handheld devices. Accordingly, the present invention can take the form of an entirely hardware embodiment, an entirely software (including firmware, resident software, micro-code, etc.) embodiment, or an embodiment containing both software and hardware aspects. Embodiments of the present invention can take the form of computer program products on computer-usable or computer-readable storage medium having computer-usable or computer-readable program code means embodied in the medium for use by or in connection with an instruction execution system. In the context of this document, a computer-usable or computer-readable medium can be any means that can contain, store, communicate, propagate, or transport the program for use by or in connection with the instruction execution system, apparatus, or device.

The computer-usable or computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which program code is printed, as the program code can be electronically captured, via, for instance, optical scanning of the paper or other medium, then compiled, interpreted, or otherwise processed in a suitable manner if necessary, and then stored in a computer memory.

Computer program code for carrying out operations of the present invention may be written in object oriented programming languages (e.g., JAVA®, Smalltalk or C++) and/or may also be written in conventional procedural programming languages (e.g., "C"). However, embodiments of the present invention do not depend on implementation with a particular programming language. Program code for providing data to respective handheld devices according to embodiments of the present invention may execute on one or more other data processing systems which perform the functions of a "central server" described herein.

The present invention is described below with reference to block diagram and/or flowchart illustrations of methods, apparatus (systems) and computer program products according to an embodiment of the invention. It is understood that each block of the block diagram and/or flowchart illustrations, and combinations of blocks in the block diagram and/or flowchart illustrations, can be implemented by computer program instructions. These computer program instructions may be provided to a processor of a central server (12, FIG. 1) and/or each handheld device (14, FIG. 1) to produce a machine, such that the instructions, which execute via the respective processor, create means for implementing the functions specified in the block diagram and/or flowchart block or blocks.

These computer program instructions may also be stored in a computer-readable memory that can direct a central server (12, FIG. 1) and/or each handheld device (14, FIG. 1) to function in a particular manner, such that the instructions stored in the computer-readable memory produce an article of manufacture including instructions which implement the function(s) specified in the block diagram and/or flowchart block or blocks.

The computer program instructions may also be loaded onto the central server (12, FIG. 1) and/or each handheld device (14, FIG. 1) to cause a series of operational steps to be performed to produce a computer implemented process such that the instructions which execute provide steps for implementing the functions specified in the block diagram and/or flowchart block or blocks.

It should be noted that, in some embodiments of the present invention, the functions noted in the flowchart blocks may occur out of the order noted in the figures. For example, two blocks shown in succession may in fact be executed substantially concurrently or the blocks may sometimes be executed in reverse order, depending on the functionality involved. Furthermore, in certain embodiments of the present invention, such as object oriented programming embodiments, the sequential nature of the flowcharts may be replaced with an object model such that operations and/or functions may be performed in parallel or sequentially.

FIG. 1 is a block diagram that illustrates a data processing system 10 according to embodiments of the present invention. The illustrated data processing system 10 is implemented in a hospital or other medical facility and includes a central server 12 that is configured to obtain patient data from various data sources 18 (e.g., legacy and other types of data systems), reformat the data for display within the displays of handheld devices, and serve the reformatted data to handheld devices 14 via docking stations 16 in various locations within the hospital. In the illustrated embodiment, docking stations 16 are located in the Emergency Room (ER), Intensive Care, Geriatric Ward, Psychiatric Ward, Maternity Ward, and Pediatric Ward. However, it is understood that docking stations 16 may be located in any area of a medical facility, without limitation.

Embodiments of the present invention are not limited to handheld devices. Any data display device may is be utilized to implement embodiments of the present invention. Moreover, embodiments of the present invention are not limited to the use of docking stations for communicating with data display devices. Various ways of transferring data (e.g., via packet switching technology) to a handheld device (or other data display device) may be utilized.

According to embodiments of the present invention, outbound HL7 data streams from existing hospital data systems are assimilated into a common format for submission into a "staging database" under the control of a central server 12. The staging database supports device-independent data exchange with pull/push synchronization to the handheld devices 14 via the respective docking stations 16. An exemplary staging database is the Oracle® 8i RDBMS, available from Oracle Corporation, Redwood Shores, Calif.

According to embodiments of the present invention, the functions of the central server 12 may be performed by one or more servers, as would be understood by those skilled in the art. As such, the term "central server" is intended to include any number of data processing systems configured to obtain clinical data associated with patients from one or more data sources, reformat the data for display within handheld device displays, and transmit the reformatted patient data to one or more docking stations 16. As used herein, the term "clinical data" is intended to include various patient information, laboratory results, medication lists, diagnostic reports (radiology, microbiology, pathology, etc.), dictated reports, etc., without limitation.

According to embodiments of the present invention, a handheld device 14 is periodically placed within a respective docking station 16 that is in communication with the central server 12 such that the handheld device 14 can receive updated data from the central server 12. The various functions of the central server 12, docking stations 16 and handheld devices 14, as well as various modes of communications therebetween, are described in commonly owned U.S. patent application Ser. No. 09/776,484, the disclosure of which is incorporated herein by reference in its entirety as if set forth fully herein.

Handheld devices 14 according to embodiments of the present invention are typically small enough to be held by one hand and typically include such features as handwriting recognition, pop-up keypads and number pads, communication software for Internet access, and the ability to hook up to a docking station 16 to exchange information therewith. Various types of handheld devices may be utilized in accordance with embodiments of the present invention. The term "handheld device" is intended to include, but is not limited to, PDAs, radiotelephones, web-enabled radiotelephones, and other mobile/wireless devices. Exemplary handheld devices which may be utilized in accordance with embodiments of the present invention include, but are not limited to, devices available from Handspring, Inc., Mountain View, Calif.; Palm, Inc., Santa Clara, Calif.; Compaq Computer Corporation, Houston, Tex.; Hewlett-Packard Company, Palo Alto, Calif.; IBM, Armonk, N.Y.; HandEra, Inc., Des Moines, Iowa; Psion PLC, London, UK; Nokia Corporation, Keilahdentie, Finland; Ericsson, Inc., New York, N.Y.; and Motorola, Inc., Schaumburg, Ill.

Figure 2:
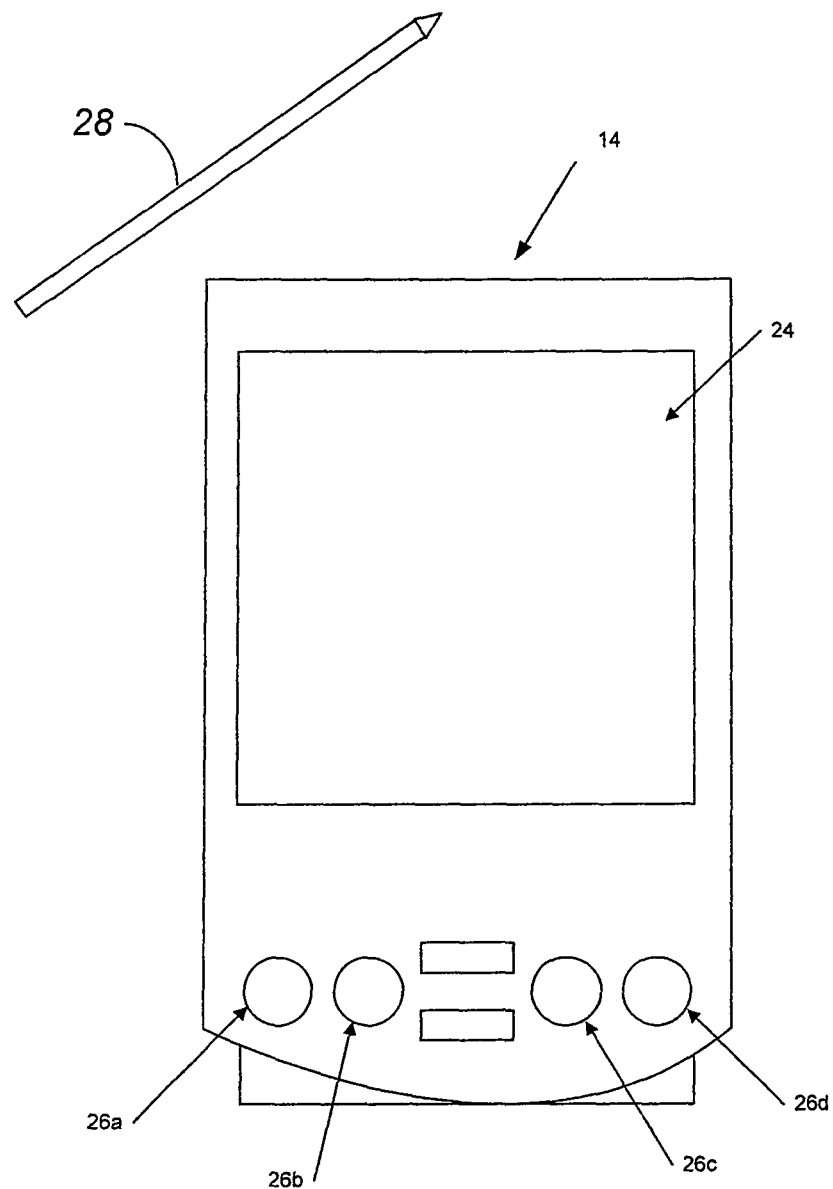
FIG. 2 illustrates an exemplary handheld device having a display screen within which user interfaces according to embodiments of the present invention may be displayed.

FIG. 2 depicts an exemplary handheld device 14, which includes a display screen 24, operational buttons 26a, 26b, 26c, 26d and a stylus 28. A more extensive keyboard (not shown) may also be included as an attachment or as an integrated part of the handheld device 14. The display screen 24 utilizes "touch screen" technology, which allows a user to interact with the display screen 24 using, for example, their finger or the stylus 28.

Referring to FIGS. 3-20, graphical user interfaces (GUIs) that are configured to be displayed within a touch screen display of a handheld device 14 according to embodiments of the present invention are illustrated. As used throughout, the term "user activation" with respect to a GUI control shall include user "touching" (e.g., via a finger or stylus) of the GUI control, which causes the GUI control to perform one or more functions.

Figure 3:
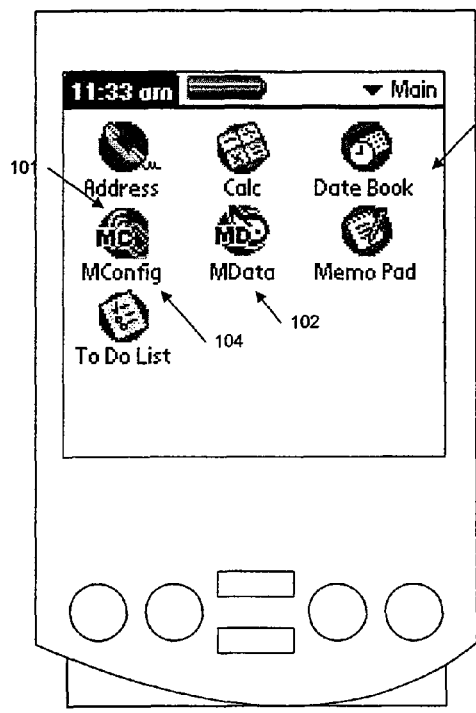

In FIG. 3, an initial GUI 100 that a user will see when a handheld device implementing embodiments of the present invention is turned on is illustrated. The illustrated initial GUI 100 includes a plurality of GUI controls 101, each of which is configured to perform one or more functions when activated (e.g., touched) by a user. GUI control 102, entitled "MData", is configured to initiate display of various GUIs according to embodiments of the present invention. GUI control 104, entitled "MConfig", is configured to initiate the viral transmission/dissemination and configuration of software as will be discussed in detail below. The remaining GUI controls are configured to perform other handheld device functions as would be understood by those skilled in this art.

Figure 4:
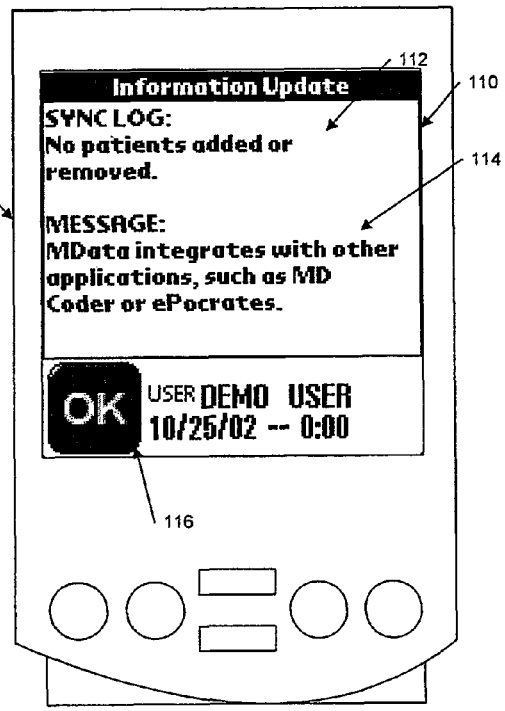

Referring to FIG. 4, GUI 110, entitled "Information Update", is displayed in response to user activation of GUI control 102 (FIG. 3) entitled "MData". In the area labeled "SYNC LOG" 112, the GUI 110 informs the user that patients and/or user lists have been added/removed during the last communication with the central server (12, FIG. 1). In the area labeled "MESSAGE" 114, the GUI 110 provides useful updates and user tips. This feature can also be accessed from other GUIs described below via user activation of GUI control 134 ("Circle 'i' ").

Figure 5:
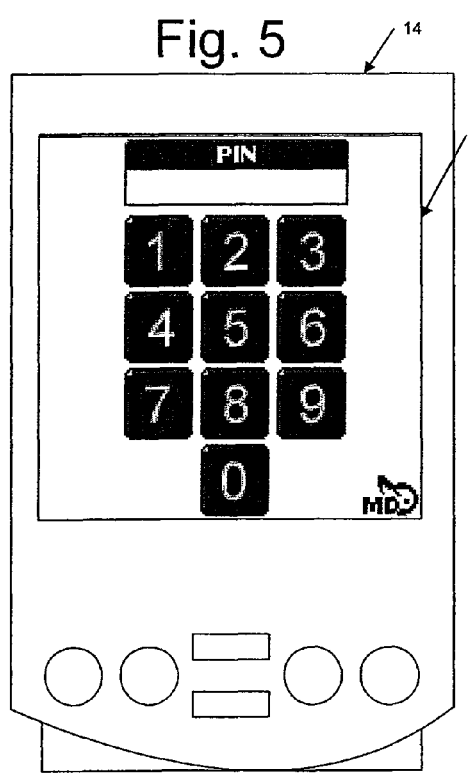

User activation of GUI control 116 ("OK") in the GUI 110 presents the user with the GUI 120 illustrated in FIG. 5. GUI 120 requires a user to enter a personal identification number (PIN) in order to proceed to access patient data. According to embodiments of the present invention, GUI 120 may be configured to appear at predetermined time intervals during the display of patient data. For example, the user may be required to re-enter his/her PIN every hour. GUI 120 can also be accessed from other GUIs described below by activating GUI control 137 ("Launch Button", FIG. 6).

Figure 6:
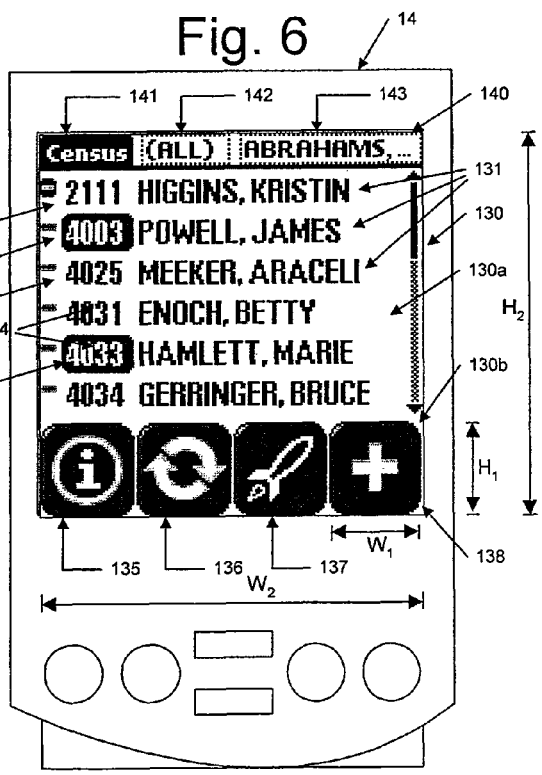

Referring to FIG. 6, a GUI 130 referred to as the "Census" screen is displayed and contains a list of patient names 131 for which a user wishes to access data. The GUI 130 is divided into adjacent first and second portions 130a, 130b, and the list of patient names 131 is displayed within the first portion 130a of the GUI 130 as illustrated. Each displayed patient name 131 identifies a patient who is being treated within a medical facility. Each patient name 131 is configured to display various clinical data stored within the handheld device for the respective patient in response to a user activating the displayed patient name 131.

Location information (e.g., hospital room number) 132 for each patient within a medical facility is displayed within the first portion 130a of the GUI 131 adjacent each respective patient name 131. The medical facility location information 132 identifies a location of a respective patient within a medical facility. The GUI 130 is configured to display an indication 133 that new clinical data for a patient is available. In the illustrated embodiment, an indication 133 of new clinical data is displayed adjacent a respective patient name by highlighting the medical facility location information 132 for a respective patient. In the illustrated embodiment, an indication 133 of new clinical data is displayed for patients Powell and Hamlett. An indication 133 of new clinical data for a patient can be provided in any of various ways, including highlighting, color changes, and/or separate icons.

A GUI control 134 (illustrated in GUI 130 as a "minus" sign) is displayed within the GUI first portion adjacent each respective patient name 131. Each GUI control 134 is configured to remove a respective patient name 131 from the displayed list. For example, the GUI control 134 adjacent to patient Higgins is configured to remove patient Higgins from the displayed list of names 131 when activated by a user.

The illustrated GUI 130 includes a plurality of GUI controls 135-138 displayed within the second portion 130b thereof. GUI control 135, when activated by a user, displays information about new clinical data for patients displayed within the GUI 130. GUI control 135 also may be configured to display other updated information and user tips. GUI control 136, when activated by a user, initiates a process for downloading clinical data from a plurality of medical facility data sources to the handheld device within which the GUI 130 is displayed. For example, a user activates GUI control 136 after placing the handheld device within a docking station (16, FIG. 1) to receive clinical data from the central server (12, FIG. 1).

GUI control 137, when activated by a user, is configured to launch other applications within the handheld device displaying the GUI 130. For example, applications such as browsers, spreadsheets, and the like may be launched by activating GUI control 137. In addition, GUI control 137 may be configured to launch applications that are context-sensitive with information displayed within the first portion 130a of the GUI 130.

GUI control 138, when activated by a user, is configured to add patient names to the displayed list of patient names 131. Upon activating GUI control 138, GUI 150 is displayed (FIG. 10) and within which a user is required to enter the medical record number of a patient to be added within the "MR Num" field 151. In addition, the user can add this patient to any of the physician lists he/she is following by placing a check mark in one or more of the check mark fields (152, FIG. 10).

Referring back to FIG. 6, GUI 130 also includes a menu bar 140 along an upper edge of the GUI first portion 130a, as illustrated. The illustrated menu bar 140 includes first, second and third areas 141, 142, 143. The word "Census" is displayed within the first area 141 of the menu bar 140. When a user activates the first area 141, an "Options" menu 144 is displayed, as illustrated in FIG. 7.

The Options menu 144 contains various GUI controls that a user can activate to invoke various functions. For example, the "Show Hidden Patients" GUI control 145a, when activated by a user, displays names of patients that have been previously removed from the displayed list in the GUI 130 of FIG. 6. The "Don't Show Hidden Patients" GUI control 145b, when activated by a user, removes the names of patients that have been previously removed from the displayed list in the GUI 130 of FIG. 6. The "Sort by Name" GUI control 144c, when activated by a user, sorts the displayed list of patient names in the GUI 130 by patient name. The "Sort by Room" GUI control 144d, when activated by a user, sorts and displays patient names in the GUI 130 by patient room number (i.e., physical location of patient). The "Find" GUI control 144e, when activated by a user, allows a user to find a patient within the list of patient names displayed within the GUI 130 of FIG. 6. The "Change PIN" GUI control 144f, when activated by a user, allows a user to change his/her PIN.

Figures 7, 8:
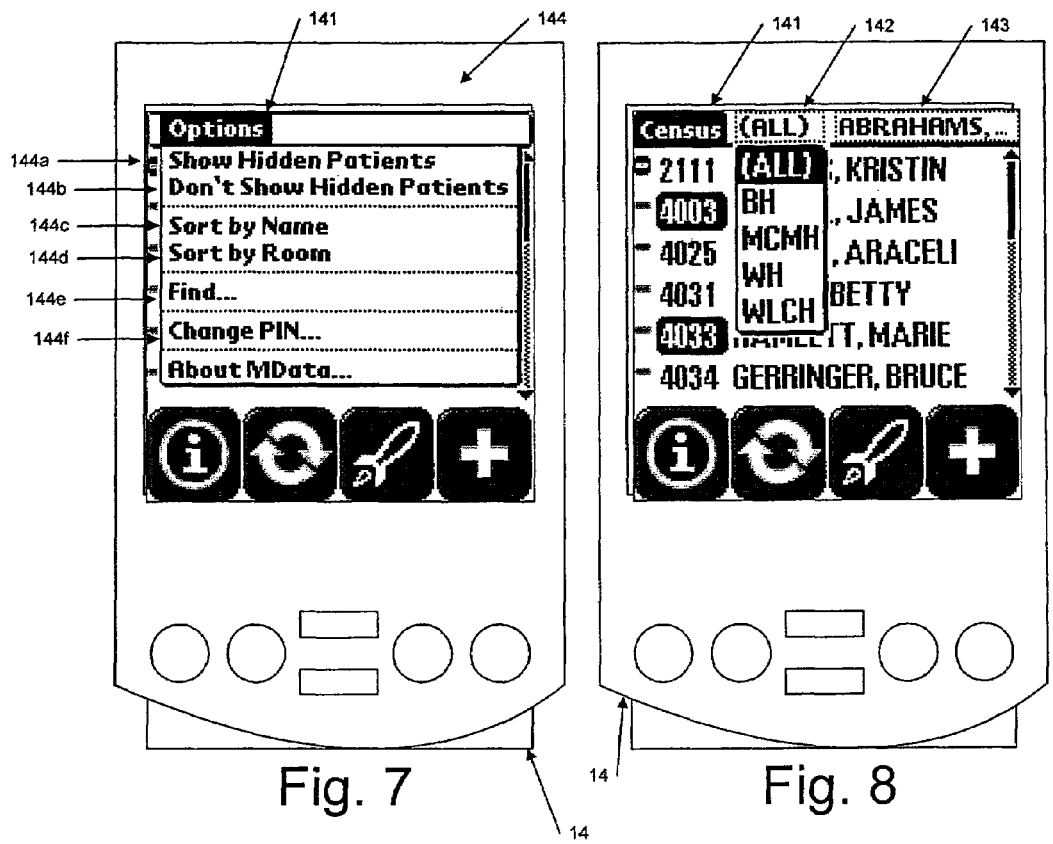

Referring to FIG. 8, the second area 142 of the menu bar 140 of GUI 130 (FIG. 6) is a GUI control that, when activated by a user, sorts and displays the patients within the GUI 130 of FIG. 6 by medical facility. For example, for a healthcare system having multiple hospitals, the second area 142 lets a user sort patients by the hospital in which the patient resides.

Figures 9, 10:
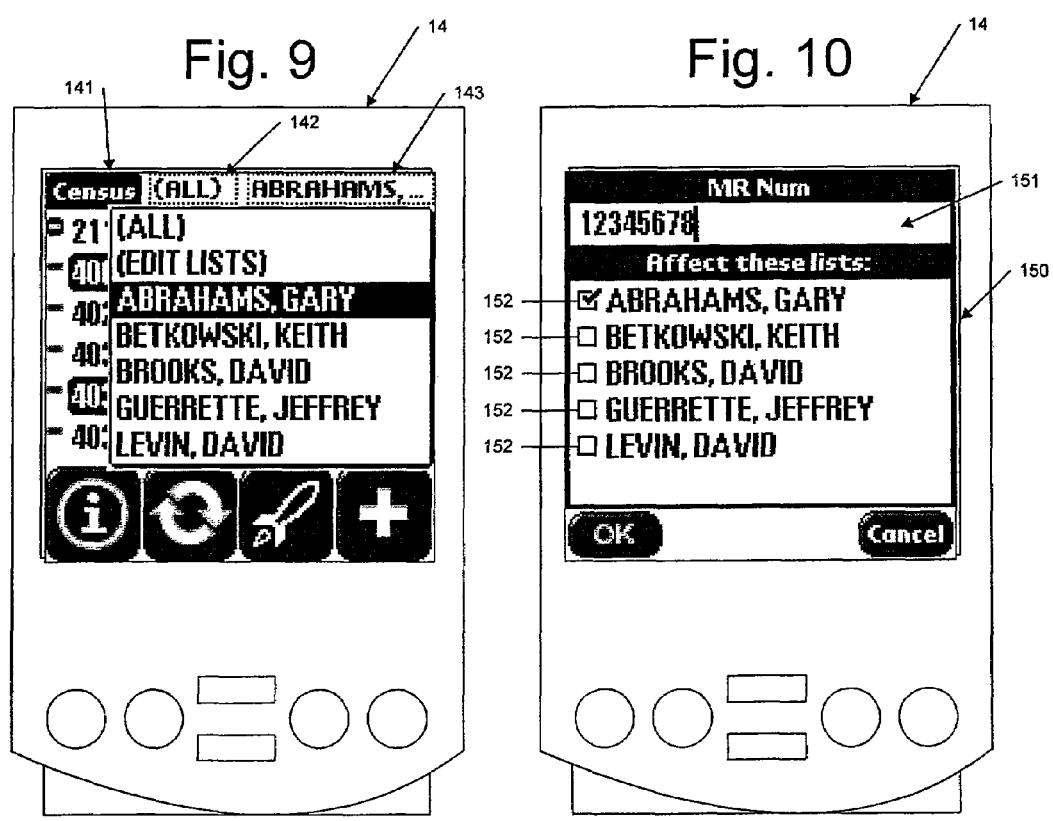

Referring to FIG. 9, the third area 143 of the menu bar 140 of the GUI 130 (FIG. 6) is a GUI control that, when activated by a user, sorts and displays the patients within the GUI 130 of FIG. 6 based upon physician (or other healthcare provider) or based upon nursing unit with which the patient is associated. Accordingly, a healthcare provider can have access to patient lists of other healthcare providers.

Referring back to FIG. 6, according to embodiments of the present invention, GUI controls 135-138 within the GUI second portion 130b are designed to be easily activated by a user's finger. As such each GUI control 135-138 has a width $W_1$ that is between about 15% and 75% of the width $W_2$ of the GUI 130, and a height $H_1$ that is between about 15% and 75% of a height $H_2$ of the display within which GUI 130 is displayed.

Figure 11:
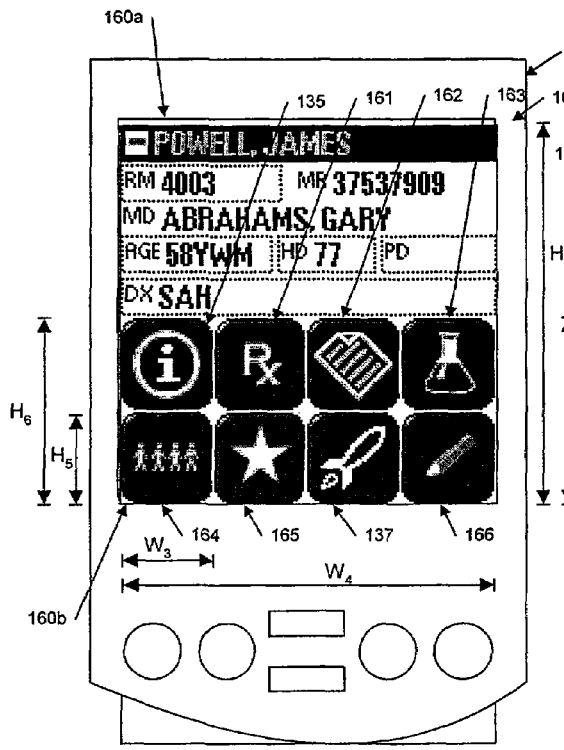

When a user activates a patient's name in the displayed list of patient names 131 in GUI 130, a GUI 160, referred to as the "Homescreen", is displayed as illustrated in FIG. 11. The illustrated GUI 160 includes adjacent first and second portions 160a, 160b. According to embodiments of the present invention, the second portion 160b has a height $H_3$ that is between about 30% and 70% of a height $H_4$ of the display within which GUI 160 is displayed.

Information associated with the respective patient is displayed within the first portion 160a of GUI 160. The displayed patient information includes patient identification and location information. One or more fields within the first portion 160a may be responsive to user activation for displaying additional patient information. The displayed patient information includes various demographic and medical history information for the patient. Various fields within the first portion 160a are responsive to user activation for displaying additional information. These fields are indicated by dotted-line borders in the illustrated embodiment.

A plurality of GUI controls 135, 137, 161-166 are displayed within the second portion 160b. Each of the GUI controls 135, 137, 161-166 has a width $W_3$ that is between about 15% and 75% of a width $W_4$ of the second portion, and a height $H_5$ that is between about 15% and 75% of a height $H_6$ of the second portion.

GUI control 135, when activated by a user, displays information about new clinical data for the patient displayed within the GUI 160. GUI control 135 also may be configured to display other updated information and user tips.

Figure 14:
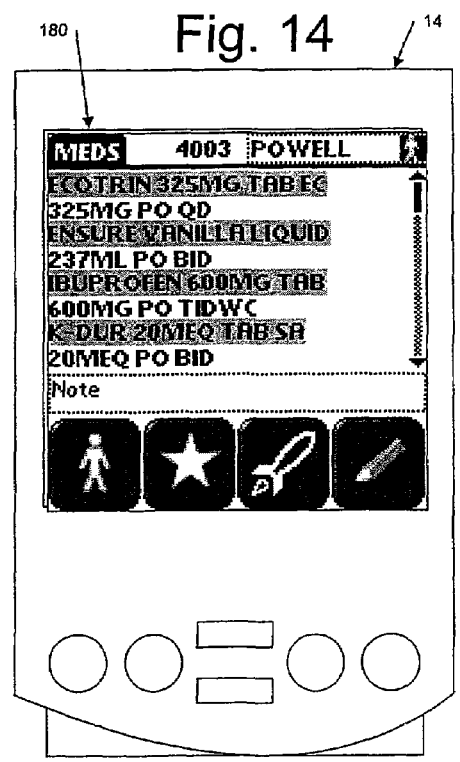

GUI control 161, when activated by a user, is configured to display a list of medications ordered for the patient via the GUI 180 illustrated in FIG. 14. In the illustrated GUI 180 (FIG. 14), the name of each medication prescribed to the patient is highlighted, and the dosage schedule is displayed beneath it. According to embodiments of the present invention, user "tapping" on the name of a medication will "drill down" to a more detailed screen expanding on all the abbreviations listed, and any special instructions for the medication (FIG. 15).

Figure 15:
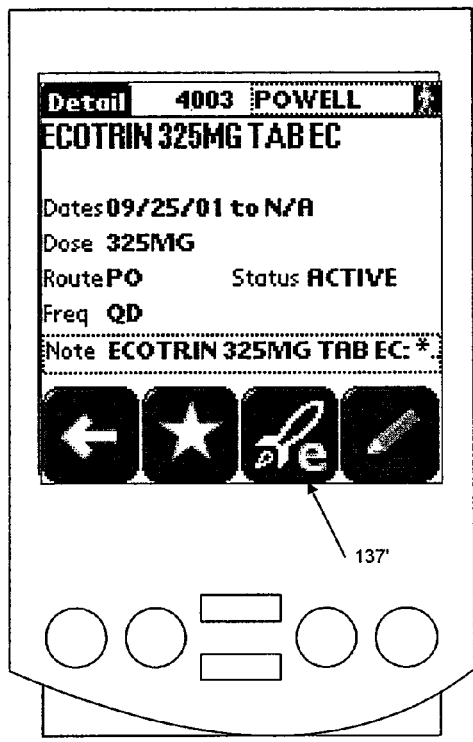

The detailed view of the medication in FIG. 15 may be extracted from a hospital information system (HIS) according to embodiments of the present invention. The illustrated layout is intentionally varied in font size and prominence in order to emphasize key pieces of information that are clinically important. GUI control 137', when activated by a user, is configured to launch a commercial drug guide, going directly to the entry for the displayed medication.

Figure 13:
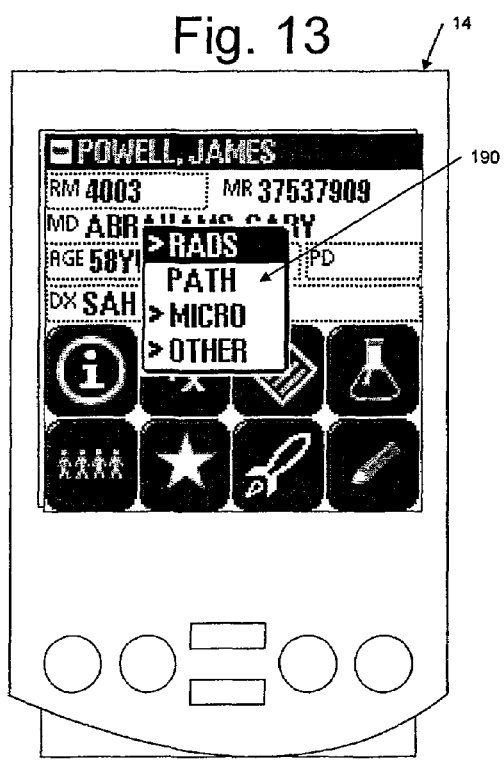

Referring back to FIG. 11, GUI control 162, when activated by a user, is configured to display text reports and/or categories of text reports for a patient, as illustrated in FIG. 13. In FIG. 13, a pop-up list 190 of text reports is illustrated according to embodiments of the present invention. An exemplary text report is a radiology report produced as a result of a clinical test such as a chest x-ray.

Figure 12:
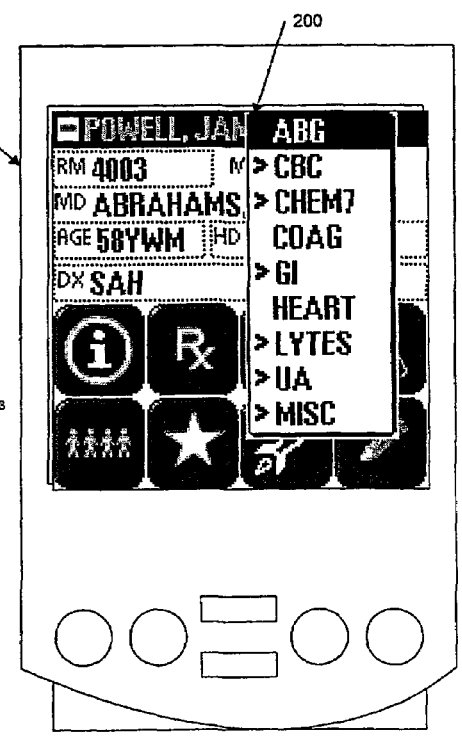

Referring back to FIG. 11, GUI control 163, when activated by a user, is configured to display a list of important categories of clinical tests for a patient, as illustrated in FIG. 12. In FIG. 12, a pop-up list 200 of clinical tests is illustrated according to embodiments of the present invention.

Referring back to FIG. 11, GUI control 164, when activated by a user, is configured to return a user to the GUI 130 of FIG. 6.

Referring back to FIG. 11, GUI control 165, when activated by a user, is configured to display a listing (referred to as the "Hotlist") 230 (FIG. 18) of clinical test results for a patient (e.g., lab results, radiology results, etc.) for the last 24/48/72 hours (or for any designated time periods). The order these results are displayed in and eligible duration of results is configurable under the "Range" tab 232.

Referring back to FIG. 11, GUI control 137, when activated by a user, is configured to launch and/or link to one or more third party applications. For example, in FIG. 17, a pop-up list 210 is displayed upon user activation of GUI control 137. Within the displayed pop-up list 210, the function "Edit Links" lets a user add/remove applications and/or links that can be launched from the pop-up list. The function "Lock & Exit" enables PIN security on the handheld device. For example, upon activating "Lock & Exit", a user can return device operation and display to the device operating system. Subsequent viewing of patient data will require the user to re-enter his/her PIN. The function "Appointment" creates a datebook entry for that specific patient on the native handheld device, and the user is able to select a day.

Figure 16:
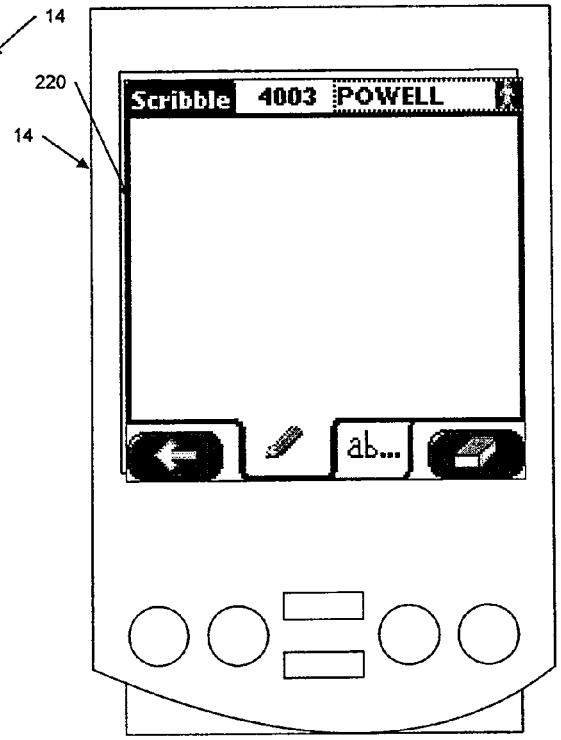
Figure 17:
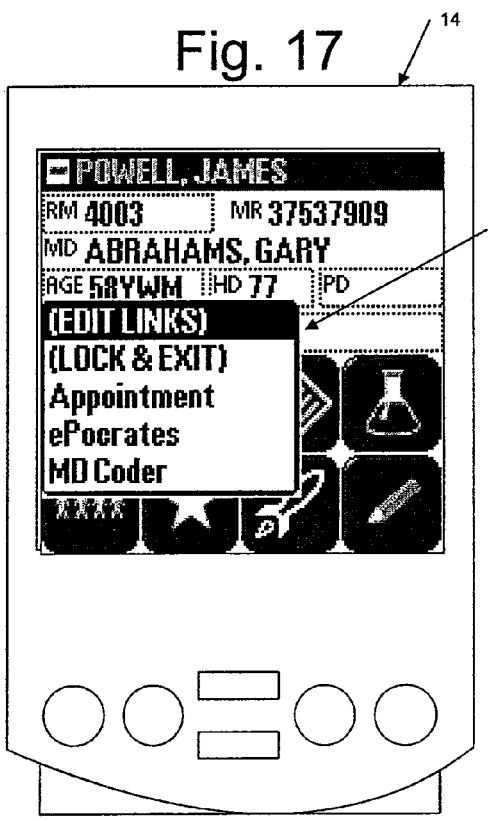
Figure 18:
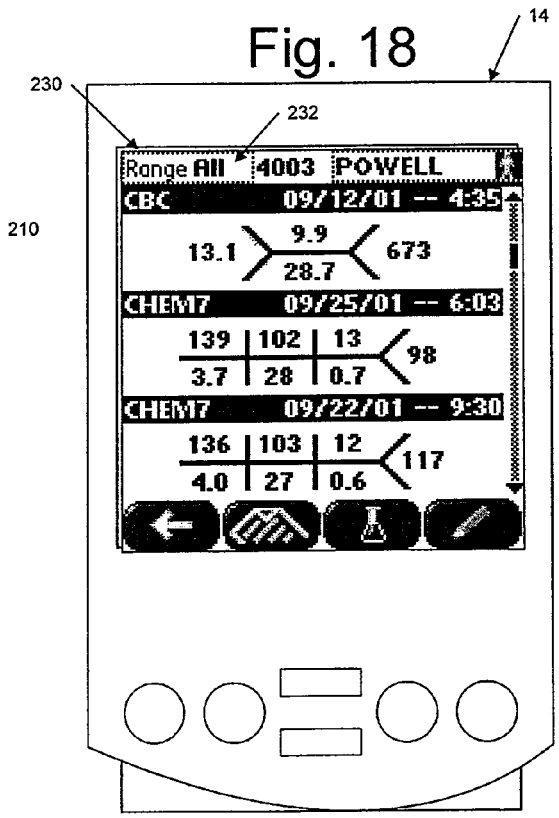

Referring back to FIG. 11, GUI control 166, when activated by a user, is configured to open up a free-draw scratch pad 220 (FIG. 16). User notes entered via scratch pad 220 are configured to remain associated with the particular patient (name displayed in upper right), and only on the particular user handheld device.

According to embodiments of the present invention, a pop-up explanation for any of the above-described GUIs, and portions thereof, is available when a user taps and holds a particular GUI area for a designated time period (e.g., one second or more). second. FIG. 19 illustrates an exemplary pop-up explanation 240 for a particular GUI according to embodiments of the present invention.

FIG. 20 illustrates a GUI 250 that enables a user to "virally" beam software for displaying patient information according to embodiments of the present invention to other handheld devices. Once another user has been beamed an application, the user must receive authorization to access the central server (12, FIG. 1) to be able to access patient data via the GUIs described above with respect to FIGS. 3-19.

Figure 21:
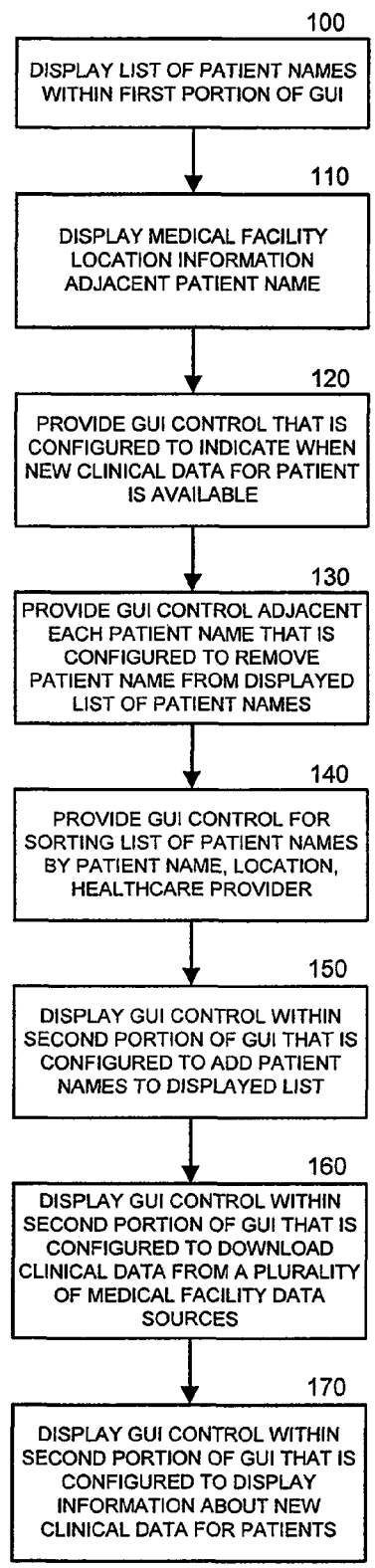
FIGS. 21-22 are flowcharts that illustrate operations for obtaining and displaying medical record information within handheld device displays according to embodiments of the present invention.

Referring now to FIG. 21 operations for displaying the GUI 130 of FIG. 6 within a touch screen display of a handheld device according to embodiments of the present invention are illustrated. A list of patient names is displayed within a first portion of a GUI (Block 100). Each displayed patient name identifies a patient within a medical facility and is responsive to user touching. Clinical data stored within the handheld device and associated with a patient is displayable upon user activation of a respective displayed patient name. Medical facility location information for a patient is displayed adjacent a respective patient name (Block 110). The medical facility location information identifies a location of a respective patient within a medical facility. A GUI control that is configured to indicate when new clinical data for a patient is available is provided (Block 120). According to embodiments of the present invention, such an indication is displayed adjacent a respective patient name. A GUI control is displayed within the GUI first portion adjacent each respective patient name that is configured to remove a patient name from the displayed list of patient names (Block 130). A GUI control is provided that is configured to sort the list of patient names by at least one of patient name, patient location within a medical facility, medical facility, and healthcare provider (Block 140).

A GUI control that is configured to add patient names to the displayed list of names is displayed within a second portion of the GUI adjacent the display first portion (Block 150). A GUI control that is configured to download clinical data from a plurality of medical facility data sources is displayed within the second portion of the GUI (Block 160). A GUI control that is configured to display information about new clinical data for patients is displayed within the second portion of the GUI (Block 170). Each of the GUI controls within the second portion of the GUI has a width that is between about 15% and 75% of a width of the display, and a height that is between about 15% and 75% of a height of the display.

Figure 22:
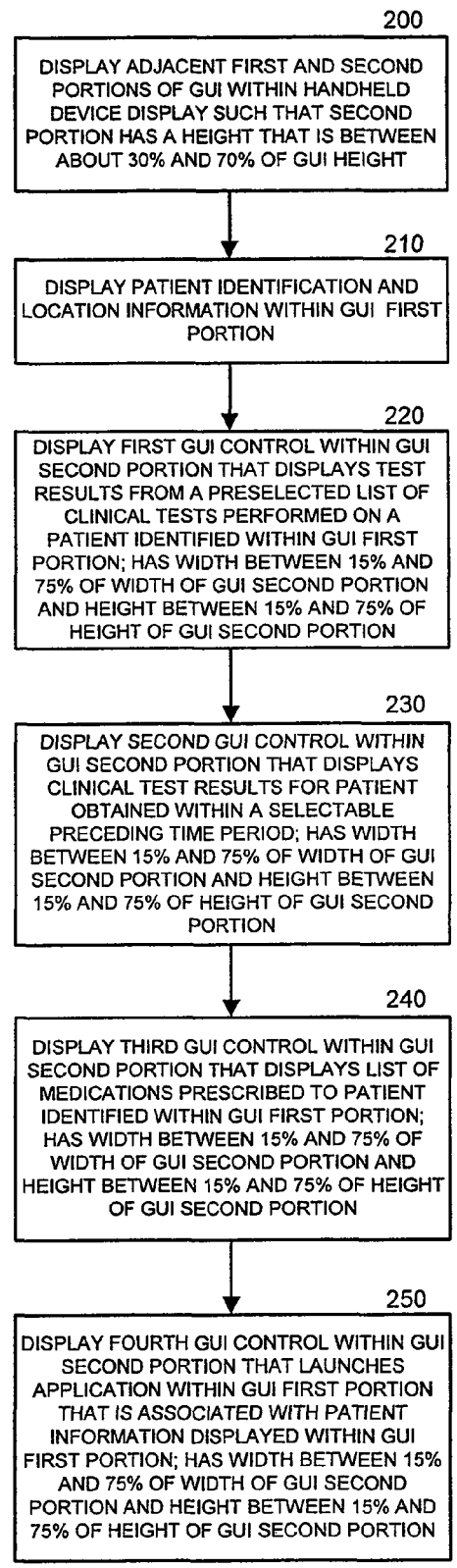

Referring now to FIG. 22 operations for displaying the GUI 160 of FIG. 11 within a touch screen display of a handheld device according to embodiments of the present invention are illustrated. Adjacent first and second portions of a GUI are displayed within a handheld device display, wherein the second portion has a height that is between about 30% and 70% of a height of the GUI (Block 200). Information for a respective patient is displayed within the first portion and includes patient identification and location information (Block 210). At least some of the displayed information is responsive to user touching for displaying additional patient information. A first GUI control is displayed within the second portion, and is responsive to user touching for displaying test results from a preselected list of clinical tests performed on a patient identified within the first portion of the GUI (Block 220). A second GUI control is displayed within the second portion, and is responsive to user touching for displaying clinical test results for the patient obtained within a selectable preceding time period (Block 230). A third GUI control is displayed within the second portion, and is responsive to user touching for displaying a list of medications prescribed to the patient identified within the first portion of the GUI (Block 240). A fourth GUI control is displayed within the second portion, and is responsive to user touching for launching an application within the first portion that is associated with the patient information displayed within the first portion. Each of the first, second, third, and fourth GUI controls has a width that is between about 15% and 75% of a width of the second portion, and a height that is between about 15% and 75% of a height of the second portion.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A non-transitory computer readable medium comprising instructions that when executed by a processor executes a process comprising:

displaying a graphical user interface (GUI) within a touch screen display of a handheld device, wherein the handheld device is configured to download and store clinical data associated with patients in medical facilities, wherein the clinical data for each patient includes data from a plurality of records;

displaying a list of patient names within a first portion of the GUI, wherein each displayed patient name identifies a patient within a medical facility, wherein each displayed patient name is responsive to user touching, and wherein clinical data stored within the handheld device and associated with a patient is displayable upon user touching of a respective displayed patient name;

displaying a plurality of GUI controls within a second portion of the GUI, the GUI controls being pictograms;

displaying medical facility location information for a patient adjacent a respective patient name, wherein the medical facility location information identifies a location of a respective patient within a medical facility; and displaying an indication that new clinical data for a patient has been obtained in a syncing operation, wherein the indication is displayed adjacent a respective patient name in the list of patient names and includes highlighting only the medical facility location information.

2. The non-transitory computer readable medium of claim 1, wherein one of the GUI controls in the second display portion is responsive to user touching for adding patient names to the displayable list of patient names, wherein the GUI control has a width that is between about 15% and 75% of a width of the display, and wherein the GUI control has a height that is between about 15% and 75% of a height of the display.

3. The non-transitory computer readable medium of claim 1, wherein one of the GUI controls in the second display portion is responsive to user touching for downloading clinical data from a plurality of medical facility data sources to the handheld device, wherein the GUI control has a width that is between about 15% and 75% of a width of the display, and wherein the GUI control has a height that is between about 15% and 75% of a height of the display.

4. The non-transitory computer readable medium of claim 1, wherein one of the GUI controls in the second display portion is responsive to user touching for displaying information about new clinical data for patients via the handheld device, wherein the GUI control has a width that is between about 15% and 75% of a width of the display, and wherein the GUI control has a height that is between about 15% and 75% of a height of the display.

5. The non-transitory computer readable medium of claim 1, further comprising instructions for displaying a GUI control within the display first portion adjacent each respective patient name, wherein each GUI control is responsive to user touching for removing patient a respective patient name from the displayed list of patient names.

6. The non-transitory computer readable medium of claim 1, further comprising instructions for displaying a GUI control responsive to user touching for sorting the list of patient names by at least one of patient name, patient location within a medical facility, medical facility, and healthcare provider.

7. A method of displaying a graphical user interface (GUI) within a touch screen display of a handheld device, wherein the handheld device is configured to download and store clinical data associated with patients in medical facilities, wherein the clinical data for each patient includes data from a plurality of records associated with the patient, wherein the method comprises:

displaying a list of patient names within a first portion of the GUI, wherein each displayed patient name identifies a patient within a medical facility, wherein each displayed patient name is responsive to user touching, and wherein clinical data stored within the handheld device and associated with a patient is displayable upon user touching of a respective displayed patient name;

displaying a plurality of GUI controls within a second portion of the GUI, the GUI controls being pictograms;

displaying medical facility location information for a patient displayed adjacent a respective patient name, wherein the medical facility location information identifies a location of a respective patient within a medical facility; and displaying an indication that new clinical data for a patient is has been obtained in a syncing operation, wherein the indication is displayed adjacent a respective patient name in the list of patient names and includes highlighting only the medical facility location information.

8. The method of claim 7, wherein one of the GUI controls in the second display portion is responsive to user touching for adding patient names to the displayable list of patient names, wherein the GUI control has a width that is between about 15% and 75% of a width of the display, and wherein the GUI control has a height that is between about 15% and 75% of a height of the display.

9. The method of claim 7, wherein one of the GUI controls in the second display portion is responsive to user touching for downloading clinical data from a plurality of medical facility data sources to the handheld device, wherein the GUI control has a width that is between about 15% and 75% of a width of the display, and wherein the GUI control has a height that is between about 15% and 75% of a height of the display.

10. The method of claim 7, wherein one of the GUI controls in the second display portion is responsive to user touching for displaying information about new clinical data for patients via the handheld device, wherein the GUI control has a width that is between about 15% and 75% of a width of the display, and wherein the GUI control has a height that is between about 15% and 75% of a height of the display.

11. The method of claim 7, further comprising displaying a GUI control within the display first portion adjacent each respective patient name, wherein each GUI control is responsive to user touching for removing a respective patient name from the displayed list of patient names.

12. The method of claim 7, further comprising displaying a GUI control responsive to user touching for sorting the list of patient names by at least one of patient name, patient location within a medical facility, medical facility, and healthcare provider.

13. A data processing system, comprising:
   a server configured to serve clinical data associated with patients in one or more medical facilities, wherein the clinical data for each patient includes data from a plurality of records associated with the patient;
   a handheld device comprising a touch screen display, wherein the handheld device is configured to download and store clinical data from the server; and
   a graphical user interface (GUI) displayed within the handheld device touch screen display, wherein the GUI comprises:
      a list of patient names displayed within a first portion of the GUI, wherein each displayed patient name identifies a patient within a medical facility, wherein each displayed patient name is responsive to user touching, and wherein clinical data stored within the handheld device and associated with a patient is displayable upon user touching of a respective displayed patient name;
      medical facility location information for a patient displayed adjacent a respective patient name, wherein the medical facility location information identifies a location of a respective patient within a medical facility; and
      a plurality of GUI controls displayed within a second portion of the GUI, the GUI controls being pictograms;
      means for displaying an indication that new clinical data for a patient has been obtained in a syncing operation, wherein the indication is displayed adjacent a respective patient name in the list of patient names and includes highlighting only the medical facility location information.

14. The data processing system of claim 13, wherein one of the GUI controls in the second display portion is responsive to user touching for adding patient names to the displayable list of patient names, wherein the GUI control has a width that is between about 15% and 75% of a width of the display, and wherein the GUI control has a height that is between about 15% and 75% of a height of the display.

15. The data processing system of claim 13, wherein one of the GUI controls in the second display portion is responsive to user touching for downloading clinical data from a plurality of medical facility data sources to the handheld device, wherein the GUI control has a width that is between about 15% and 75% of a width of the display, and wherein the GUI control has a height that is between about 15% and 75% of a height of the display.

16. The data processing system of claim 13, wherein one of the GUI controls in the second display portion is responsive to user touching for displaying information about new clinical data for patients via the handheld device, wherein the GUI control has a width that is between about 15% and 75% of a width of the display, and wherein the GUI control has a height that is between about 15% and 75% of a height of the display.

17. The data processing system of claim 13, further comprising a GUI control displayed within the display first portion adjacent each respective patient name, wherein each GUI control is responsive to user touching for removing patient a respective patient name from the displayed list of patient names.

18. The data processing system of claim 13, further comprising a GUI control responsive to user touching for sorting the list of patient names by at least one of patient name, patient location within a medical facility, medical facility, and healthcare provider.

* * * * *